(12) United States Patent
Meek et al.

(10) Patent No.: US 6,979,313 B1
(45) Date of Patent: Dec. 27, 2005

(54) MEDICAL DEVICE WITH ELASTOMERIC BULB

(75) Inventors: Roger Howard Meek, Essex (GB); David Evans, Essex (GB)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/720,309

(22) PCT Filed: Jun. 25, 1999

(86) PCT No.: PCT/EP99/04421

§ 371 (c)(1),
(2), (4) Date: Apr. 9, 2001

(87) PCT Pub. No.: WO99/66976

PCT Pub. Date: Dec. 29, 1999

(30) Foreign Application Priority Data

Jun. 25, 1998 (EP) .................................. 98/03892

(51) Int. Cl.[7] ............................................. A61M 29/00
(52) U.S. Cl. ................................ 604/98.01; 604/99.03
(58) Field of Search ....................... 604/96.01, 98.01, 604/99.02, 99.01, 99.03, 99.04, 264, 523, 604/544; 606/192–196

(56) References Cited

U.S. PATENT DOCUMENTS

| | | | |
|---|---|---|---|
| 3,190,291 A | | 6/1965 | Foley |
| 3,275,001 A | * | 9/1966 | Rosecrans ................ 604/98.01 |
| 3,599,620 A | | 8/1971 | Balin |
| 3,602,226 A | * | 8/1971 | Ericson ................... 604/98.01 |
| 3,675,658 A | * | 7/1972 | Taylor ..................... 604/98.01 |
| 4,007,738 A | | 2/1977 | Yoshino |
| 4,018,231 A | * | 4/1977 | Wallace .................. 128/207.15 |
| 4,116,201 A | * | 9/1978 | Shah ...................... 128/207.15 |
| 4,140,127 A | | 2/1979 | Cianci et al. |
| 4,181,140 A | | 1/1980 | Bayham et al. |
| 4,248,236 A | | 2/1981 | Linder |
| 4,340,049 A | | 7/1982 | Munsch |
| 4,462,430 A | | 7/1984 | Anthony et al. |
| 5,014,407 A | | 5/1991 | Boughten et al. |
| 5,085,656 A | | 2/1992 | Polaschegg |
| 5,152,747 A | | 10/1992 | Olivier |
| 5,273,542 A | | 12/1993 | Blake, III |
| 5,534,228 A | | 7/1996 | Wesseler |

(Continued)

FOREIGN PATENT DOCUMENTS

DE 3100442 9/1982

(Continued)

Primary Examiner—Nicholas D. Lucchesi
Assistant Examiner—Matthew F. DeSanto
(74) Attorney, Agent, or Firm—Kirkpatrick & Lockhart Nicholson Graham LLP

(57) ABSTRACT

In a pre-filled Foley catheter for urine drainage, the conventional clip for releasing sterile water from a bulb (21) at the proximal end of the catheter, to fill the anchor bulb (20) at the distal end of the device, is replaced by a plug (25) which has an annular portion connected to a thin stem (27) by a circle of weakness. Snapping the stem (27) from the annulus provides a tactile signal through the opaque latex lumen that the catheter has been actuated. There is no separate clip to be disposed of. The interface between the latex and the plug remains undisturbed. Further improvement in the shelf-life and convenience of use of the catheter is delivered by the use of a sleeve, which can be of shrink-wrap material, around the bulb (21) and optionally also around the drain coupling (15) of the catheter. Apparatus for placing the plug and the sleeve is also described.

21 Claims, 5 Drawing Sheets

U.S. PATENT DOCUMENTS

| | | |
|---|---|---|
| 5,908,409 A | 6/1999 | Rinehart et al. |
| 6,119,697 A | 9/2000 | Engel et al. |

FOREIGN PATENT DOCUMENTS

| | | |
|---|---|---|
| DE | 3324699 | 12/1984 |
| DE | 3330148 | 3/1985 |
| DE | 3837779 | 2/1991 |
| DE | 4116474 | 11/1992 |
| EP | 0177859 | 4/1986 |
| EP | 0193406 | 9/1986 |
| EP | 0377035 | 5/1994 |
| EP | 0584317 | 4/1996 |
| GB | 1573482 | 8/1980 |

\* cited by examiner

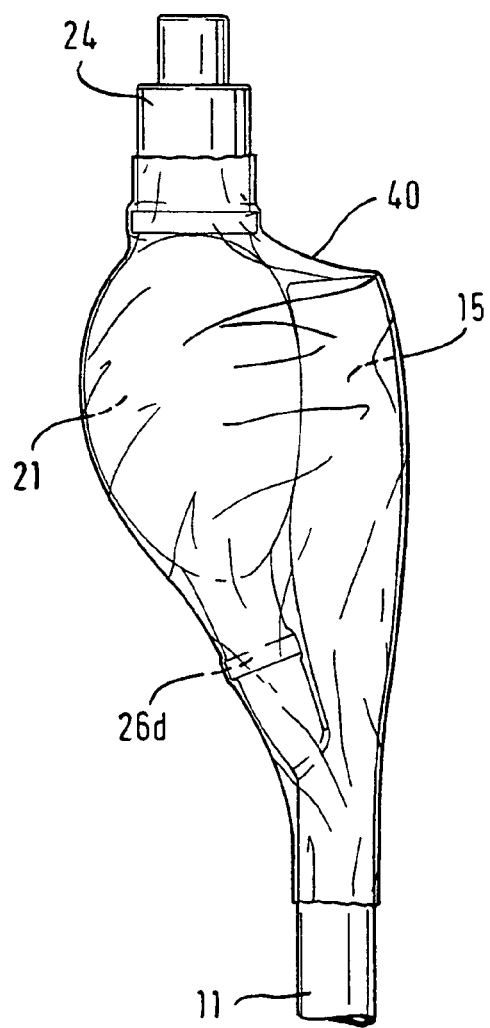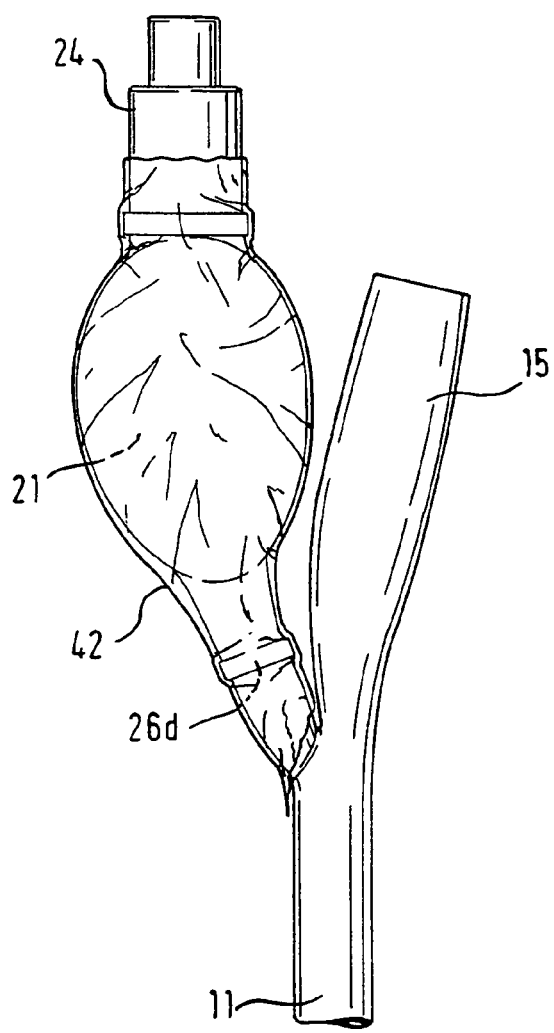

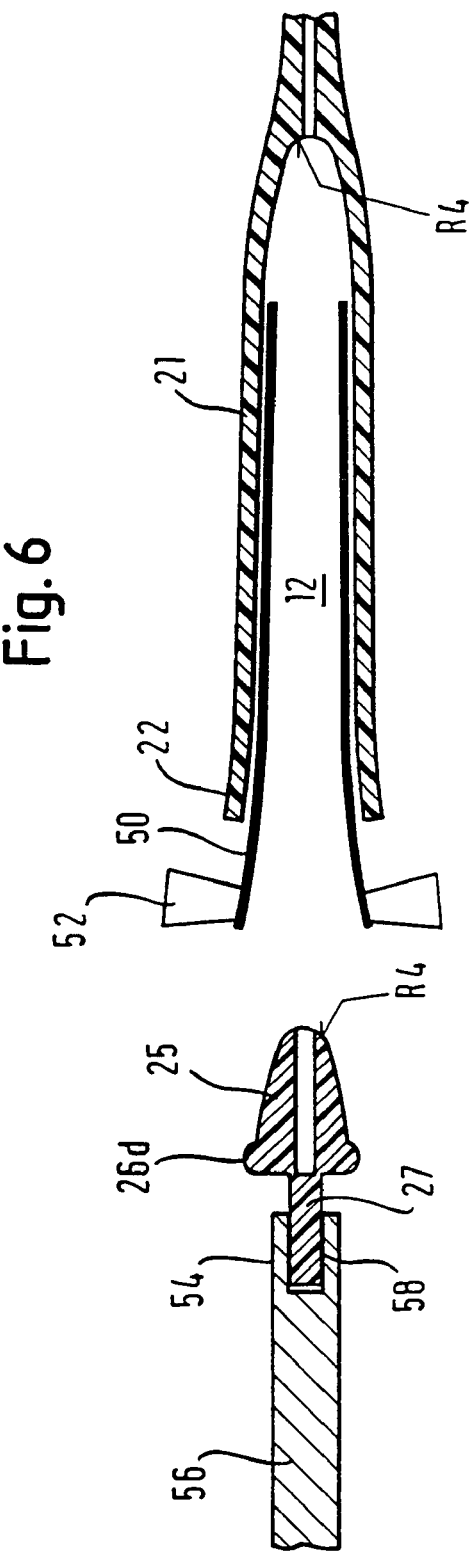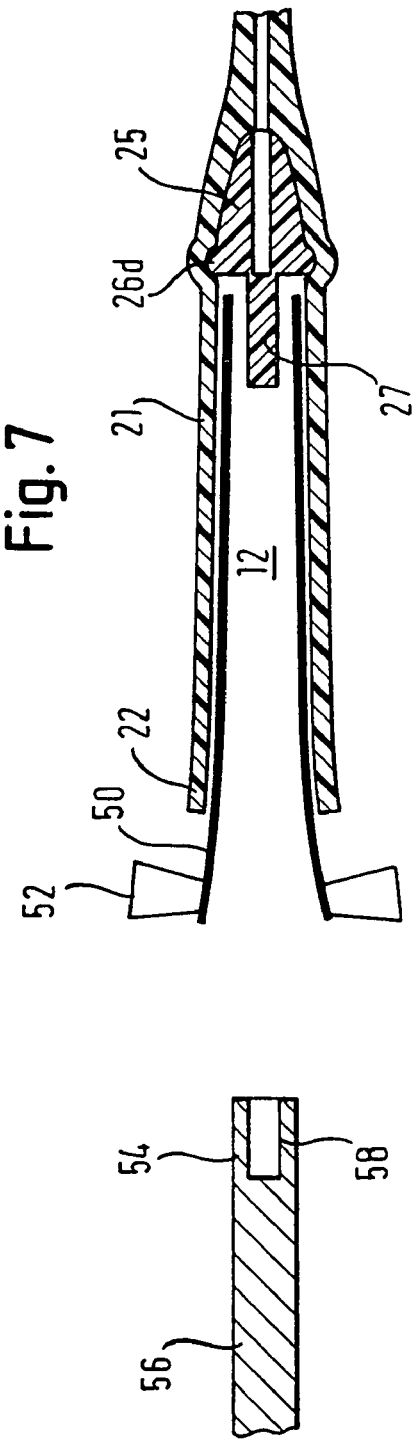

MEDICAL DEVICE WITH ELASTOMERIC BULB

TECHNICAL FIELD

A pre-filled Foley catheter can be regarded as one example of a medical device with a proximal end and a distal end, an elastomeric bulb at the proximal end for storing fluid under pressure and a fluid acceptor at the distal end and a lumen connecting the bulb and the acceptor for flow of fluid from the bulb to the acceptor when the device is used, and including a control device at the proximal end of the lumen to prevent said fluid flow until said flow is desired. It is in this class of medical devices that the present invention is to be found.

BACKGROUND

The Foley catheter is a catheter device usually made out of elastomeric material, which is for urine drainage and which is installed with its distal end in the bladder of the patient. When the distal end of the catheter has been advanced into the bladder, sterile water is caused to flow along a lumen from the proximal to the distal end of the catheter, there to fill a balloon at the distal end of the catheter. This balloon retains the distal end of the catheter in the bladder and allows a second lumen in the catheter shaft, open to the bladder at the distal end of the shaft, to drain urine from the bladder to the proximal end of the catheter.

In a pre-filled Foley catheter, such as shown in U.S. Pat. No. 3,602,226 the device includes a reservoir of sterile water in the proximal end of the device, and a clip over the shaft of the catheter at its proximal end, which clip prevents the sterile water from flowing from the distended reservoir bulb along the lumen to the distal end of the catheter. The person placing the catheter is required to hold the catheter in the desired disposition relative to the body of the patient, and then remove the clip and squeeze the reservoir bulb, in order to inflate the balloon. It would be desirable to provide an improved device for preventing fluid flow from the reservoir to the balloon until it is desired to do so. U.S. Pat. Nos. 3,275,001 and 3,675,658 disclosed the use of internal plugs instead of clip.

Achievement of satisfactory shelf-life for pre-filled Foley catheters has proved to be a challenge. Common elastomeric material, such as latex, is not entirely impermeable to the passage of water. Accordingly, the water in the distended bulb reservoir of elastomeric material can escape through the wall, given enough time. In order to achieve a satisfactory shelf-life (18 to 24 months) it has been proposed to cover the outside of the reservoir bulb with a coating of material more resistant to passage of water than latex. Nevertheless, residual problems remain some of which are discussed in the U.S. Pat. No. 3,602,226.

One such problem is that the coating tends to crack. This reduces the resistance to escape of water and can adversely affect appearance. Another problem is to achieve satisfactory continuity of the coating around the clip at the distal end of the bulb, and the customary filler valve at the proximal end of the bulb. Even then, there is potential for water to escape from the bulb by flowing lengthways along the elastomeric material of the wall of the bulb, until it has passed the distal and proximal ends of the waterproof coating material.

The thickness of latex catheters made by a conventional dipping process is always liable to vary, and this variation can prejudice the goal of reliable sealing with an external moulded clip. With a conventional U-shaped one-piece clip, and latex walls of uncertain thickness, there is some potential for the clip to damage the latex lumen wall.

SUMMARY OF THE INVENTION

The invention may be incorporated in embodiments that may include one or more of the following objects, features and characteristics.

An object of the present invention is to achieve greater certainty, during the manufacture of pre-filled Foley catheters, that the catheter will deliver a satisfactory shelf life.

A further object of the present invention is to provide a pre-filled catheter which lends itself to easy actuation, with a single manipulation (like removal of the conventional clip) being sufficient to achieve the result that all fluid in the reservoir flows to the distal end balloon cavity.

Another object of the invention is to improve the design of the catheter so that its manufacture is streamlined, its packaging and storage made more compact and reliable, and its appearance made more attractive.

Thus, in accordance with a first aspect of the present invention, there is provided a medical device of the type identified above, and which is characterized in that said control device comprises a plug which blocks the lumen at its proximal end and includes a parting line, which enables the plug to be parted into two separate parts, by manual manipulation from outside the lumen, such parting having the effect of opening up fluid communication along the lumen from the elastomeric bulb to the balloon to fill the balloon.

Advantageously, once the plug is parted, there is no need for the person installing the catheter to manipulate any longer the plug or lumen.

Additionally the stress distribution in the wall of the bulb at the neck at its distal end is much more uniform with a plug than with the customary clip. An enhanced ability to predict patterns of stress and strain at the balloon neck should in turn allow better waterproofing in the distal neck region.

Moreover, provision of a parting line avoids the need to disturb the interface between plug and lumen. This is especially advantageous with latex lumens, or other lumens created by dipping, in which the wall thickness varies, because actuation of the control device need not involve any surface in contact with the lumen wall. Where the lumen wall thickness varies, so will the elastic performance, and when the elastic performance varies, there will be unpredictability in the manipulation of any surfaces constrained elastically by the lumen wall surface.

Conventionally, a Foley catheter of latex is moulded with a narrow lumen (of the order of 0.8 mm diameter) and a proximal bulb inner diameter much larger. Thus, in another aspect of the invention, the distal neck of the bulb cavity can be molded to correspond in shape with the distal end of the plug. These complementary surfaces prevent excessive advance of the plug distally beyond the bulb neck.

Stabilisation of the interface between the lumen wall and the surfaces of the control device makes it easier to render the bulb fluid-tight in this interface zone. The medical device is much easier to pack and to handle in the terminal stages of manufacture because it lacks the bulk of an external clip.

Conventional external clips become separated from the conventional pre-filled Foley catheter, once the catheter has been installed, and one then has the task of disposing of the loose clip. With the device of the invention, the component parts of the control device are retained within the bulb.

One-handed operation of the valve requires less manual dexterity than with an external clip which has to be removed. Snapping of the plug into two pieces provides a tactile signal that the fluid passage has been opened up.

With opaque lumen material, such as latex, the plug cannot be seen, so such a tactile signal is especially valuable with opaque materials.

In another aspect of the invention, the use of the plug facilitates avoidance of potential difficulties in coating the interior of the reservoir, as may be desired to waterproof the reservoir to minimize liquid loss during storage. By placement of a plug in the distal neck of the bulb, before the coating process the coating material will be precluded from blocking the lumen. A coating of proofing material on the external surface of the plug ought not to have any adverse effect on the operation of the plug device.

In another embodiment, it is envisaged that the plug device might carry with it a skirt or cylinder of waterproof material, to serve as the fluid-resistant wall of the bulb, or an inner waterproof surface coating of the wall of the bulb, the skirt or cylinder being gathered at the proximal end of the bulb, and fitted around the customary bulb filler valve. Cakes are decorated using an icing sugar mixture which is extruded through an icing nozzle, itself set in the neck of an icing bag. The other end of the bag is held closed by the hand of the user. The contemplated arrangement of plug and skirt might resemble an arrangement of icing nozzle and icing bag, with the filler valve closing the end of the skirt remote from the plug.

The control of flow of fluid in a lumen, using a device in the lumen which is separable into two parts in order to allow fluid flow, is not in itself new. Such an arrangement is disclosed in, for example, GB-A-1573482 and U.S. Pat. No. 4,007,738 published Feb. 15, 1977. It is to be noted, however, that the proposal of the present invention allows the control device to be placed such that it extends proximally into the interior of the bulb. This provides more room for displacement of one part of the control device relative to the other, and for eliminating elastic stresses in a lumen wall which might otherwise act to bring the two displaced parts of the control device back into their original sealing disposition relative to each other. Depending on the materials used and the dimensions of the plug and lumen walls, locating the control device partly within the bulb may assist in delivering many of the attractive technical effects of the present invention.

In a further aspect the present invention provides a medical device which is a drainage catheter having first and second lumens, with the first lumen serving as a drainage lumen and having a fluid inflow port at its distal end and a fluid drain coupling at its proximal end. The second lumen serves to convey inflating fluid from a fluid supply element at the proximal end of the device to a fluid acceptor balloon at the distal end. The fluid supply element and fluid drain coupling are arranged side by side at the proximal end of the coupling, and the device is characterised by a sleeve which extends around both the fluid drain coupling and the fluid supply element.

Normally, the fluid supply element will be an elastomeric bulb which is destined to be inflated with the inflating fluid. In that case, the sleeve would be of a material which is more impervious to the inflating fluid than is the elastomeric material of the bulb, so that the presence of the sleeve has the effect of slowing the rate of loss of fluid radially outwardly from the bulb through the wall thickness of the bulb.

Although this is the normal situation, it is envisaged that the provision of a sleeve around both the fluid drain coupling and the fluid supply element could have other advantages independent of reducing fluid loss during storage of a pre-filled device. For example, in the case where the device is made of material which does not readily accept printed text, or in a case where it is desired that there should be no printed text on the device as such, the sleeve material could be selected as suitable for use as a printing substrate, and could receive printed matter which serves to inform those handling the device, until such time as the device is put into use, at which point the sleeve would be removed.

It is particularly envisaged that the technical feature of a sleeve, which characterises the second aspect of the invention, is used in combination with the technical feature of a lumen plug which parts into two pieces, characteristic of the first aspect of the invention. In particular, a urinary drainage catheter, such as a Foley catheter, which incorporates a reservoir pre-filled with liquid to inflate the distal bulb of the catheter, and which is made, as conventionally, with latex rubber material, benefits from an enhanced shelf life both by the provision of a sleeve around the reservoir bulb at the proximal end of the catheter, and the provision of a plug instead of a conventional external lumen clip, because the sleeve over the bulb works more effectively when there is no clip on the external surface of the catheter adjacent the reservoir bulb. This is because it is easier to arrange the sleeve for full effectiveness when the surface it covers is without discontinuities, and when the sleeve is not subject to localised stresses caused by the external clip.

In this way, the sleeve and plug work together to enhance the shelf life of the device.

In this connection, inclusion of the fluid drain coupling alongside the fluid supply element inside the sleeve will not appreciably reduce the effectiveness of the sleeve in slowing down the rate of loss of fluid through the wall of the reservoir bulb. This is because both elements can be made with surface topographies made up of gentle curves and out of relatively soft materials which therefore deform relatively easily to conform to the embrace of a sleeve applied using shrink wrapping techniques. However, placing the sleeve around both the fluid drain coupling and the fluid supply element can deliver the technical effect that the device is packed in a more compact and orderly way, which facilitates further manufacturing processing and packaging of the device, and improves the visual attractiveness of the device to those who purchase and use it. It also provides a packaging over the fluid drain coupling (which in present devices is not sleeved) and a vehicle for carrying printed matter.

Both aspects of the invention are particularly applicable to medical devices made of latex rubber, especially urine drainage catheters made of latex rubber. However, both aspects of the invention will also be useful with devices made of other materials. One of these may be silicone rubber, an alternative material for urine drainage catheters.

Normally, the fluid received at the distal end of the catheter will be water, that is, sterile water, but the invention is not restricted to fluids which are liquids. Fluids which are gases may also be of interest.

The plug control device is conveniently formed as an annulus of material with a proximal end face and a distal end face and a bore extending between the two end faces. Coaxial with the annulus is a stem, blocking the bore in the annulus, until the plug is parted into two separate parts, these two separate parts being the annulus and the stem. Conveniently, the plug is formed of synthetic polymeric material, injection moulded as a single component, with a circle of weakness, constituting the parting line, between the annulus and the stem, at one end of the bore through the annulus. However, it can also be envisaged that the plug is formed of two components, the annulus and the stem, put together as the plug is installed in the lumen, and parted into the respective annulus and stem components, along the parting line where the two components abut one another, when the stem is manipulated from outside the device. In such a case, the stem might be friction fitted within the bore of the annulus.

Normally the stem is cylindrical and has a diameter not more than about half that of the plug at its widest point. Advantageously, the stem is not more than one third the plug diameter. In one example, the stem is 2.25 mm diameter and the plug at its widest is 7.5 mm in diameter. This leaves plenty of room around the stem to engage the stem with an injector rod to position the plug in the lumen.

Normally, the plug is advanced into the lumen from the proximal end of the lumen with its stem directed rearwardly. Normally, the open proximal end of the lumen is closed by a filler valve, and the plug is spaced some way from the filler valve, distally along the lumen. The lumen length between the filler valve and the plug contains the cavity for storing fluid under pressure, that is to say, the fluid supply element and elastomeric bulb of preferred embodiments of the present invention. Fluid is introduced through the filler valve into the lumen cavity between the filler valve and the plug, to inflate the elastomeric bulb between the valve and the plug. The valve is a check valve (not unlike one on a bicycle tyre) which resists reverse flow of the fluid in the bulb. In these respects, the reader will be informed by conventional practice in the technical field of urine drainage catheters, particularly Foley catheters. Variations of construction of the filler valve are not in themselves an aspect of the subject matter of the present invention.

BRIEF DESCRIPTION OF THE DRAWINGS

For a better understanding of the present invention, and to show more clearly how the same made be carried into effect, reference will now be made, to the accompanying drawings, in which:

FIG. 4 is a longitudinal diametral section of a catheter in accordance with FIG. 2, showing a sleeve extending around both the fluid drain coupling and the fluid supply element;

FIG. 5 is a longitudinal section, similar to that of FIG. 4, but showing a sleeve which extends only around the fluid supply element, and not around the fluid drain coupling;

FIG. 6 is a longitudinal section through apparatus for placing the plug inside the lumen of the Foley catheter; and FIG. 7 is a section like FIG. 6, but showing the plug after placement in the lumen.

DESCRIPTION OF THE PREFERRED EMBODIMENT

Figure 1:
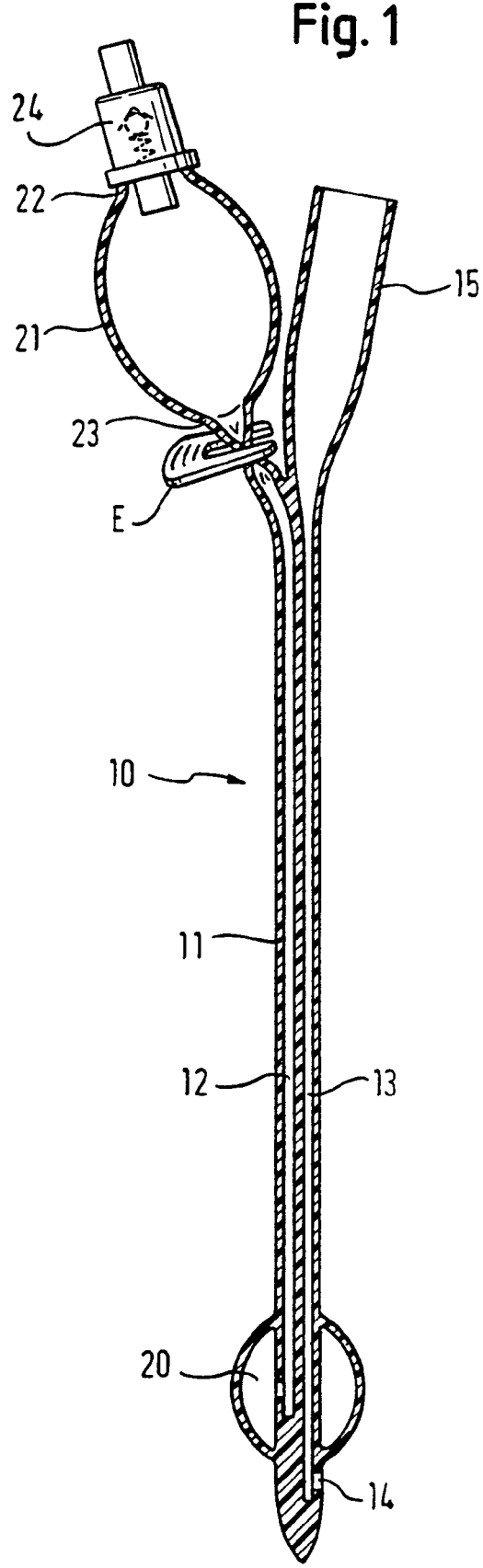
FIG. 1 is a longitudinal diametral section through a Foley catheter which is within the state of the art.

FIG. 1 shows a known pre-filled Foley catheter. The catheter 10 comprises a shaft 11 of latex rubber which defines a balloon inflation lumen 12 and a drainage lumen 13. The drainage lumen 13 extends from a distal drainage port 14 to a drainage bag coupling element 15 at the proximal end of the catheter. The inflation lumen 12 connects a chamber 20 at the distal end of the catheter, but proximal of the drainage port 14, with a reservoir bulb 21 at the proximal end of the device. In FIG. 1, both of the balloon 20 and bulb 21 are shown inflated, for the sake of clarity, but those skilled in the art will appreciate that the sterile water within the bulb 21 is not sufficient simultaneously to fill both the bulb and the balloon. The reality is that, when the bulb 21 is full, the balloon 20 is not yet inflated and, when the balloon 20 is fully inflated, the bulb 21 is deflated.

The bulb 21 has a proximal end 22 and a distal end 23. At the proximal end 22 is a conventional one-way filler valve 24 with which those skilled in the art will already be familiar. At the distal neck 23 of the bulb 21, there is a conventional external clip E to clamp together the walls of the lumen 12.

Figure 2:
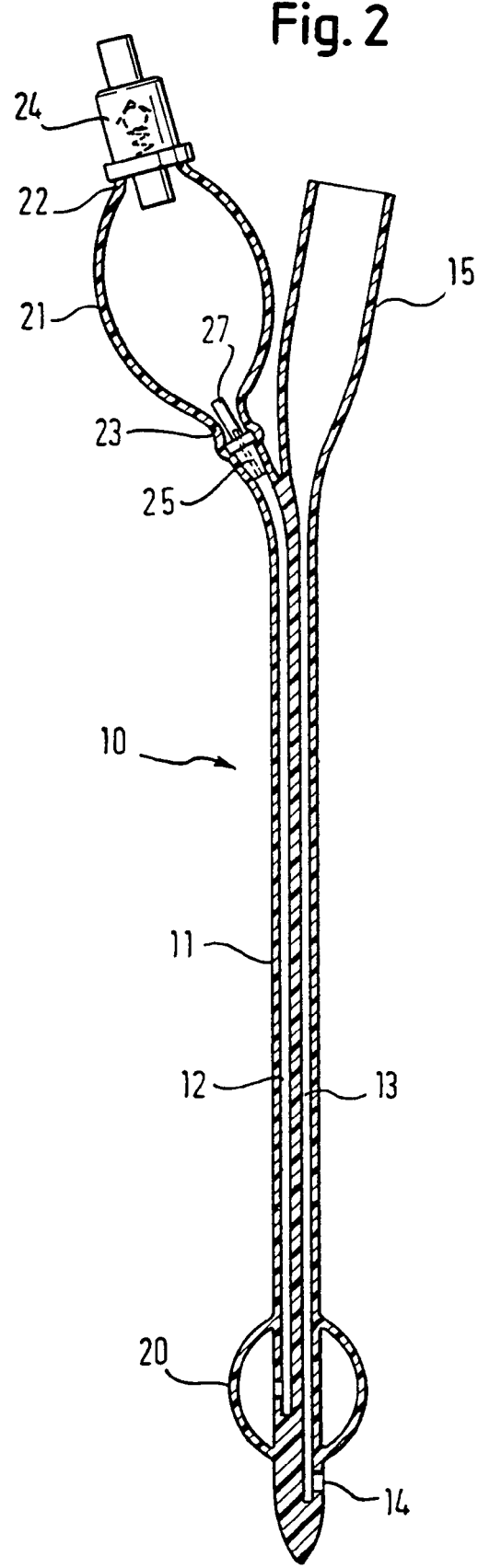
FIG. 2 is a longitudinal diametral section through a Foley catheter in accordance with the present invention.
Figure 3:
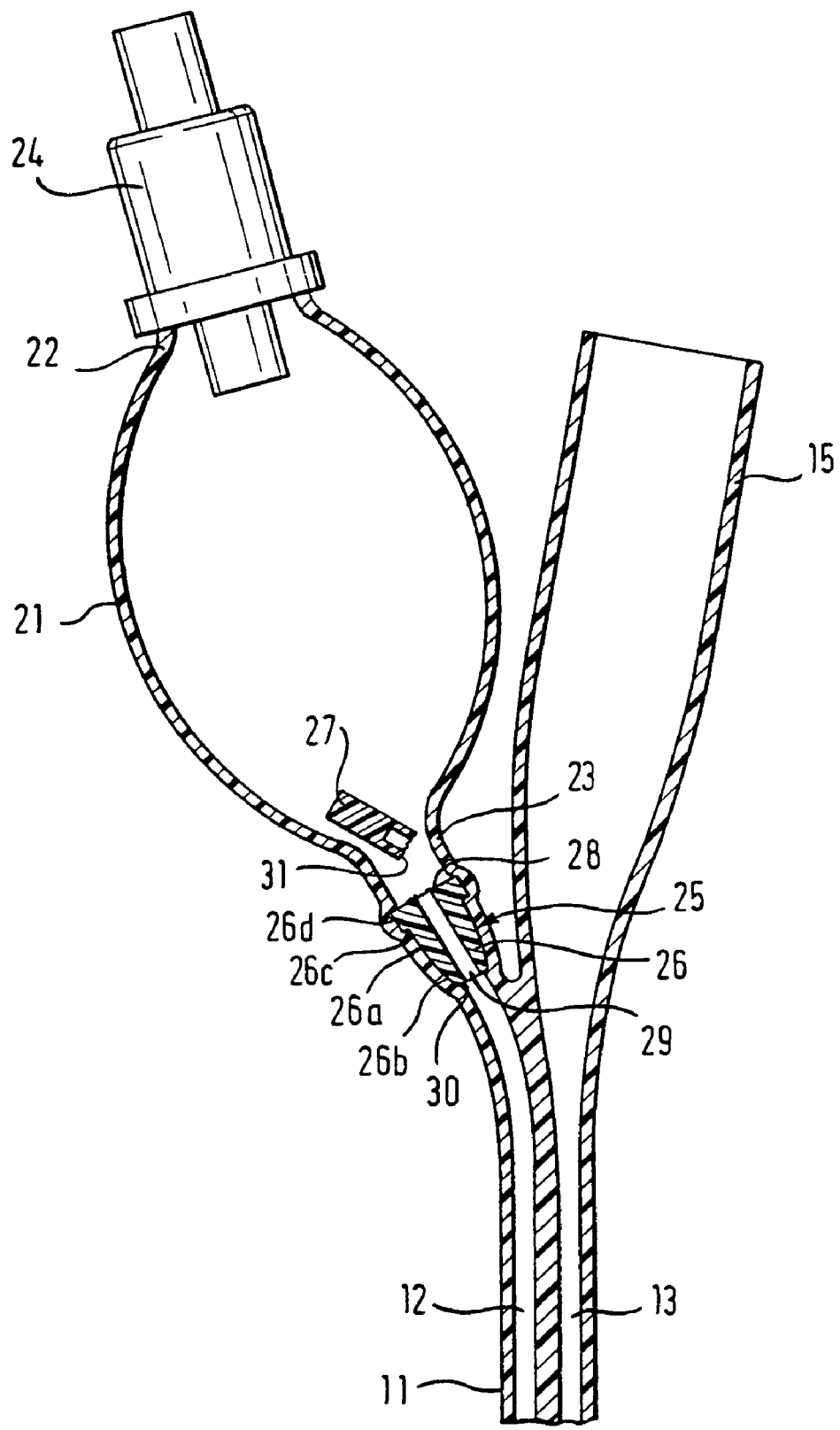
FIG. 3 is a longitudinal diametral section through the proximal end of the FIG. 2 catheter, showing the plug parted into two parts.

Turning to FIG. 2, the catheter shown in this drawing figure is identical to that of the FIG. 1 catheter, except that the external clip E has been replaced, in accordance with the invention, by a plug 25 which is a friction fit inside the lumen 12, the plug 25 being introduced distally into the lumen 12 through the interior of the bulb 21 and, in so doing, elastically deforming the material of the shaft 11 of the catheter 10. FIG. 3 shows in more detail the construction of this control device.

In FIG. 3 the control device can be seen to be made up of a tapered plug portion 26 and a solid stem portion 27 which occludes the proximal end 28 of a bore 29 which extends completely through the plug portion 26, as far as its distal end 30. The solid stem 27 is integral with the plug portion 26, but joined to it by a narrow and weak circle 31 of material around the proximal end 28 of the bore 29. The circle 31 constitutes a parting line.

The tapered portion 26 is itself made up of adjacent more or less frusto-conical portions. The larger frusto-conical portion 26a has a relatively gentle taper along the plug axis, and the smaller frusto-conical portion 26b has a relatively faster steeper taper, together giving the plug a rounded bullet nose to be advanced along the lumen to the desire location. There is a step 26c between the tapered portion of the plug and its cylindrical portion 26d of largest diameter.

The length of the large diameter cylindrical portion 26d is preferably smaller than its radius, thereby enhancing lumen sealing around this portion of the plug. The length of the plug annulus is preferably greater than its maximum diameter, which helps to keep the plug pointing in the axial direction as it is pushed from behind to advance along the lumen.

The control device is formed from synthetic polymeric material which is selected so that manual manipulation of the solid stem 27 relative to the plug portion 26 is quite sufficient to tear the polymer material at a point on the circumference of the weak circle 31, thereby allowing the stem 27 to rotate relative to the plug portion 26, with further tearing of the material around the circle 31 putting in fluid communication the bulb 21 surrounding the stem 27 with the bore 29 through the length of the plug portion 26.

Because of the softness of the bulb, and the open space between the wall surfaces of the bulb 21 surrounding the stem 27, there is great scope for manual manipulation of the bulb, from outside it, to achieve a large angle of rotation of the stem 27 relative to the plug portion 26, with consequent great certainty of putting the bulb 21 in communication with the bore 29. Nevertheless, the stem 27 may lie in the lumen 12 spaced from the bulb, if the lumen is susceptible enough to external manipulation and bending to permit the stem 27 to be snapped away from the annulus 26.

Those skilled in the art will be familiar with the conventional dimensions of a pre-filled Foley catheter. Of course, many of these are determined by the dimensions of the associated parts of the human body. The researches of the present applicant, as to what are the preferred dimensions of the plug control device, have resulted in a proposal that the control device should be constructed in accordance with the following scheme of dimensions (all in mm): the stem portion 27 has a length of 10 and a diameter of 2.2.5;. the plug portion has a length of 9 and a bore diameter of 2; the frusto-conical outer diameter range is from 5.5. to 4.3; there is a transition zone from the proximal end of the 2 mm axial bore of the plug portion, to the 2.25 mm diameter circle on the proximal end face of the plug portion, which extends distally from the proximal end face over a distance of 0.625 mm.

The bulb can be water-proofed (as is known) for example by dipping in Saran® a polyvinylidene chloride coating composition. Otherwise it could be water-proofed by, e.g. dipping or spraying it with silicone, neoprene rubber, butyl rubber or hydrophobic polyurethane. Those skilled in the art will be aware of such procedures and practices.

One suitable polymer material for the plug device is polyvinylchloride. However, there is currently prejudice against the use of PVC. High impact polystyrene is another possibility. A polyester material such as polybutyleneterephthalate may be worthy of consideration. Styreneacrylonitrile is another polymer of particular interest. The selection of polymers for medical applications is a field in which there is considerable experience. Some special factors apply, for example, gamma ray sterilisation is usual, and the polymer must obviously be able to withstand all production process steps, including sterilisation, as well as being stable enough to survive the required shelf life period in the environment in which it finds itself. Resistance to solvents, possibly acetone, may be another significant factor. Putting the bulb interior in communication with the tube should not result in any loose fragments of the control device, especially not any transport of such fragments to the fluid acceptor. Accordingly, the preferred failure mode between stem portion 27 and plug portion 26 is tearing.

Although the presently preferred embodiment involves a circle of weakness, and parting of the polymer material around the weakness circle 31, nevertheless it is contemplated that alternative embodiments, may be desirable, in which, for example, the stem portion 27 is not integral with the plug portion 26 but, rather, is a separate piece which is friction fitted with the proximal end 28 of the bore 29. If this were the case, then it might be appropriate to provide stepped or tapered portions of the proximal end of the bore 29 or the distal end of the stem 27.

Although the present invention arose out of a consideration of how to improve a specific product, the pre-filled Foley catheter, nevertheless the concept of the invention might be applicable elsewhere. In particular, the interaction of a plug stopper and a distended elastomeric reservoir of sterile fluid could be useful whenever there is need for a supply of sterile fluid from a bulb. Thus, it could be arranged that, while the plug remains intact, the fluid is safe and sterile within the bulb, and resistant to damage or decay but, upon a simple manipulation of the stem of the plug, a supply of sterile fluid is available, from the bulb, in whatever quantities and rate of flow are selected by the user, by varying the squeezing and manipulation of the elastomeric bulb.

FIGS. 4 and 5, illustrate alternatives, in accordance with the second aspect of the present invention, to coating the fluid supply element at the proximal end of the device. Instead of dipping the proximal end in a coating liquid, the proximal end is surrounded by a sleeve. This sleeve can be like the sleeve 40 of FIG. 4, embracing both the bulb 21 and the coupling element 15, or like the sleeve 42 of FIG. 5, embracing only the bulb 21 and not the coupling 15.

One way of providing the sleeve is to use stretchy material, pre-formed as a sleeve. The lumen 11 could be advanced through the sleeve, and then the sleeve restrained while the distal parts of the catheter are pulled through the sleeve, until the sleeve is stretched by the structures at the proximal end of the catheter and ends up stretched over the bulb 21 and bag connector 15, as shown in FIG. 4.

However, it is presently preferred by Applicant to pre-form the sleeve from shrink wrap material, which is 50 $\mu$m thick oriented polystyrene material. Such material, somewhat thinner, say 40 $\mu$m thick, is also seen as likely to be suitable and useful. For the conventional Foley catheters which Applicant makes, it is appropriate to use a pre-formed tube which, when flat, has a width of 45 mm and which, for use in the present invention, is cut into lengths of 90 mm, this being long enough to extend over not only the bulb 21 but also the fluid control device 25 and the distal end of the filler valve 24, as shown in FIGS. 4 and 5. Preferred is shrink wrap sleeving which includes a tear strip or tab incorporated along its length. In the particular embodiment favoured at present by applicant, this tear tab has a width of 10 mm.

Shrink wrap sleeving, of the description immediately above, is available from Decorative Sleeves Ltd, Hardwick Industrial Estate, Kings Lynn, Norfolk, England.

Although a tear tab is not essential, and although the precise location of the tear tab relative to the drain coupling 15 and fluid bulb 21 is not critically important, it is presently preferred to locate the tear strip to lie over the surface of the bulb 21, diametrically opposite from the location of the drain coupling 15.

Those skilled in the art will be familiar with techniques for printing on polystyrene film. Should it be desired, printed matter can be placed on the polystyrene tubing pre-form, before the sleeve is placed over the bulb of the catheter.

As can be seen in FIGS. 4 and 5, heat shrinkage of the shrink wrap sleeving, in a length which extends distally beyond the sealing annulus of the fluid control device 25, and proximally beyond the sealing annulus of the filler valve 24, is sufficient to place a more or less fluid-impervious coating over the bulb 21, whether the bag coupling 15 is inside or outside the shrink wrap sleeve.

As the presently favoured method of placing the shrink wrap sleeve over the catheter bulb 21, Applicant uses a vertically arranged heat shrink tunnel. Thus, the shaft 11 of the catheter is advanced through the sleeve prior to shrinking, so that the 90 mm length of the shrink sleeve lies over the catheter bulb 21 in the axial position shown in FIG. 4 or FIG. 5, and then the catheter, with the sleeve in place, is placed between two vertical conveyor belts of the heat shrink tunnel, with the proximal end of the catheter uppermost. The conveyor belts advance the catheter downwardly through the vertically arranged heat shrink tunnel and, as the proximal end of the catheter passes through the tunnel, the heat within the tunnel will cause the sleeving to shrink around the catheter bulb 21.

At the bottom end of the heat shrink tunnel, the catheter is taken from the conveyors, again to be subjected to a manual quality check before being placed into a transport box for further processing.

FIG. 6, shows schematically the presently favoured method which applicant uses to insert the fluid control device 25 into the lumen of the catheter. A plurality of long flexible fingers 50, themselves mounted at their proximal ends to a finger ring 52, are introduced into the open end 22 of the catheter lumen which is to become the elastomeric bulb 21. Radially outward movement of the fingers 50 allows the plug 25 to be advanced axially past the open end 22 of the lumen, and beyond the part of the lumen 21 which becomes the bulb, until the plug 25 reaches the part 23 of the lumen which will become the distal neck of the bulb 21. Here, the lumen narrows down, over the length of a neck-in section R4 to the diameter of the lumen in the shaft, which here is 0.8 mm.

This advancement of the plug 25 along the lumen 12 is accomplished by an engagement of a female end 54 of an engagement rod 56 arranged on the axis of the plug insertion apparatus. The stem 27 of the plug 25 is received within the bore 58 of the female engagement portion 54 of the injector rod 56.

Conveniently, the injector rod 56 is pneumatically operated. In practice, it is convenient to provide the apparatus with a foot pedal actuator for the injector rod 56, so that a human operative can arrange the lumen end 22, fingers 50 and plug 25 as desired, with delicate use of the fingers, and then achieve plug insertion in the lumen 12 using a movement of the foot to actuate the foot pedal.

The rod 56 advances the plug 25 to the position shown in FIG. 7, in which it is snugly and co-operatingly abutting the neck-in section R4 of the lumen.

Once the plug is inserted, and the injector rod 56 retracted, the fingers 50 retract to their initial disposition, enabling the open end 22 of the lumen 12 easily to be withdrawn from the fingers. The latex lumen wall is opaque, but because the prominent ring 26d of the large diameter cylindrical portion of the plug 25 distorts the latex lumen wall, as can be seen in FIGS. 2, 3, 4 and 5, the operative can check that the plug 25 is in the desired location. It will be noted that the stem 27 projects proximally into the void within the bulb 21. After this check, the partially manufactured catheter can be placed in a transport box, for onward transport and further processing.

INDUSTRIAL APPLICABILITY

The invention, in both its aspects described above, enables improvements to be made in the manufacture, storage and handling of medical devices such as Foley catheters. These improvements are appreciated not only by manufacturers and users of these devices but also, in large measure, by those who manipulate the medical devices for industrial users. The subject matter of this invention is defined by features which are technical, and the invention delivers useful technical effects.

We claim:

1. A Foley catheter (10) with a proximal end (22) and a distal end (23), an elastomeric reservoir bulb (21) at the proximal end for storing fluid under pressure and in readiness to inflate, an anchoring balloon (20) at the distal end a lumen (12) connecting the reservoir bulb and the balloon for flow of fluid from the bulb to the balloon when the device is used, and including a control device (25) at the proximal end of the lumen to prevent said flow until said flow is desired said control device (25) comprises a plug (26) which blocks the lumen at its proximal end and includes a parting line, which enables the plug to be parted into two separate parts, by manual manipulation from outside the lumen, such parting having the effect of opening up fluid communication along the lumen from the reservoir bulb (21) to the balloon (20) to fully fill the balloon wherein the plug further comprises a co-axial stem (27) and annular part (26) with a diameter at least twice that of the stem, which meet at said parting line wherein the annular part comprises a tapering portion displaying a small end and a large end, the small end being remote from the stem, wherein the annular part comprises a cylindrical portion, wherein the cylindrical portion lies between the tapering portion and the stem, in the axial direction of the plug, wherein the diameter of the cylindrical portion is greater than that of the large end of the tapering portion, including a step between the large end of the tapering portion and the cylindrical portion.

2. Device as claimed in claim 1, wherein the diameter of the annular part of the plug is at least three times that of the stem.

3. Device as claimed in claim 2 wherein the annular part comprises an annulus (26) of material with a proximal end face (30) and a distal end face (28) and a bore (29) extending between the two end faces.

4. Device as claimed in either one of claims 2 or 3, wherein said stem (27) extends proximal of the annular port, coaxially therewith and has an outside diameter substantially less than that of said annular port (26).

5. Device as claimed in claim 4 wherein the stem (27) is integral with the annular part and joined to it by a circle of weakness (31).

6. Device as claimed in claim 5 wherein the annular part and stem are together formed as only one piece of molded polymer material.

7. Device as claimed in claim 4 wherein the stem is friction fitted within the bore (29) of the annular part.

8. Device as claimed in either one of claims 1 or 2, in which the tapering portion comprises a frusto-conical or substantially frusto-conical portion which has a small end which is larger than the small end of the tapering portion.

9. Device as claimed in claim 8 wherein the tapering portion comprises first and second frusto-conical or substantially frusto-conical portions, of different cone angle, such that the diameter of the tapering portion varies along the axis at a greater rate near the small end of the tapering portion than at the large end of the tapering portion.

10. Device as claimed in claim 2, wherein the axial length of the annular part of the plug is greater than its largest diameter.

11. Device as claimed in either one of claims 1 or 2, wherein the length of the cylindrical portion is smaller than its radius.

12. Device as claimed in claim 1 wherein the bulb (21) is coated with a substance to inhibit the passage of the fluid through the wall thickness of the bulb.

13. Device as claimed in claim 12 wherein the coating is on the outside of the bulb wall thickness.

14. Device as claimed in claim 12 wherein the coating is on the inside surface of the bulb wall.

15. Apparatus as claim in claim 1 wherein the elastomeric bulb is sleeved in shrink-wrap material.

16. Apparatus as claimed in 15 wherein the permeability of the sleeve material to diffusion of water therethrough is less than that of latex rubber.

17. Apparatus as claimed in 15 wherein the shrink-wrap material is polystyrene.

18. Apparatus as claimed in 15 wherein the shrink-wrap sleeve incorporates a tear strip.

19. Device as claimed in claim 1 wherein the plug (26) carries a fluid-tight skirt membrane which extends proximally from the proximal end face of the plug.

20. Device as claimed in claim 1 in which the stem is cylindrical.

21. Device as claimed in claim 1 wherein the fluid supply element (21) has an open proximal end (22) closed by a filler valve (24).

* * * * *